United States Patent [19]

Niezink et al.

[11] Patent Number: 5,273,532
[45] Date of Patent: Dec. 28, 1993

[54] INJECTOR FOR HYPODERMICALLY IMPLANTING AN OBJECT IN A LIVING BEING

[75] Inventors: Herman Niezink, Wierden; Franciscus H. C. Benning, Almelo, both of Netherlands

[73] Assignee: Texas Instruments Incorporated, Dallas, Tex.

[21] Appl. No.: 939,789

[22] Filed: Sep. 3, 1992

[30] Foreign Application Priority Data

Sep. 3, 1991 [NL] Netherlands .................. 9101489

[51] Int. Cl.$^5$ .................................................. A61M 36/04
[52] U.S. Cl. ................................................ 604/62; 604/60
[58] Field of Search ............................... 604/57, 59–64; 606/116, 117; 221/151

[56] References Cited

U.S. PATENT DOCUMENTS

| 4,105,030 | 8/1978 | Kercso ................... | 604/63 |
| 4,223,674 | 9/1980 | Fluent et al. ........... | 604/61 |
| 4,400,170 | 8/1983 | McNaughton et al. .... | 604/62 |
| 4,597,753 | 7/1986 | Turley .................... | 604/61 |
| 4,661,103 | 4/1987 | Harman ................... | 604/62 |
| 5,002,548 | 3/1991 | Campbell et al. ....... | 604/62 |
| 5,147,295 | 9/1992 | Stewart .................. | 604/64 |

FOREIGN PATENT DOCUMENTS

| 415504 | 3/1991 | European Pat. Off. ....... | 604/60 |
| 8901858 | 2/1991 | Netherlands .............. | 604/61 |
| 8902283 | 4/1991 | Netherlands .............. | 604/61 |

*Primary Examiner*—Ralph Lewis
*Attorney, Agent, or Firm*—Rebecca A. Mapstone; James C. Kesterson; Richard L. Donaldson

[57] ABSTRACT

Injector for hypodermically implanting of an object (14) in a living being. This injector comprises a housing (13), with a hollow needle (3) which can be moved in and out from the housing (13). In the hollow needle (3) a pushing rod (9) is received, to position an object (14) in a living being after introduction of the needle (3). Near the housing (13) a locking means is provided to realize positioning of the object. In the storage position, the needle (3) is inside the housing (13). For injecting, first of all the needle (3) is moved out of the housing (13) and locked. A spring (4) is tensioned by the outward movement of the needle (3). During introduction into the animal of the needle (3), a locking means will be actuated, after which the needle (3) returns and positioning of the object (14) is realized.

4 Claims, 4 Drawing Sheets

INJECTOR FOR HYPODERMICALLY IMPLANTING AN OBJECT IN A LIVING BEING

BACKGROUND OF THE INVENTION

1. Field of the Invention

The invention relates to an injector for hypodermically implanting an object in a living being, comprising a housing accommodating a needle (holder) in such a way that it is slidable out of said housing, on which needle(holder) a spring acts, said spring being tensioned during the outward movement of the needle, with a push rod fitted in said hollow needle for conveyance of the object, with unlocking means fitted on the housing near the outlet aperture of the needle, for detecting contact with the living being and starting the positioning of the object in the living being, and with control means for moving the needle out of the housing.

2. Description of the Invention

Such an injector is known from Dutch Patent Application 8,902,283. The spring force necessary for the various actions is produced in it by means of a tensioning handle. The needle in this case is situated in the housing when in the storage position. For the implantation of an object, the injector is moved against the animal with the needle fitted in the housing. The unlocking means are thereby operated. Said unlocking means release the control means. These control means are a puller. By means of said puller, a spring-loaded slide is released, so that the needle shoots into the animal. This means that the user does not see the insertion movement of the needle into the animal, because the injector is always held against the animal. Disconnection of the needle and the slide takes place at the end of the movement of the needle into the animal. This means that the needle is moved back out of the animal, with the slide remaining in the same position. A push rod which does not make such a return movement is also connected to the slide. Due to the fact that during the implantation an object to be implanted, such as a transponder, is placed in front of the push rod, when the needle is withdrawn and the push rod remains in place, such a transponder will be placed in the animal.

A number of disadvantages are associated with the use of this device. For tensioning of the injector, energy must be supplied both for the withdrawal of the needle and for the insertion of the needle. For, only a blocking is released by the control means. The energy required in particular during insertion of the needle is very variable. One skin is easier to pierce than another skin, due to greater thickness or other circumstances, while the state of the tissue under the skin can vary widely. This means that, either a very great pre-tensioning force is needed, which on relatively easy penetration causes too great a shock and could damage the object to be implanted, or not enough force is used to ensure that the needle penetrates sufficiently into the animal in all circumstances. If there is inadequate penetration into the animal, the placing of the transponder can go completely wrong.

Another disadvantage of this device is that, if it is in the tensioned state, the needle is present under spring tension in the housing. It is extremely simple for unskilled people, and in particular children, to injure themselves by pressing the unlocking means when engaging the control means.

SUMMARY OF THE INVENTION

The present invention describes an injector for implanting objects such as an identification transponder into living beings and comprises a housing which supports a hollow needle through which the object is delivered into the living being. The hollow needle has a sharp end and a supported end connected to the housing such that the needle can slide between a retracted position and an extended position. A push rod moves inside the needle and is connected to the housing so that it is maintained in a fixed position as the needle moves from the extended position to the retracted position. A spring or biasing member is connected between the housing and the needle to urge to or move the needle toward the retracted position. A control member or lever is provided to move the needle to the extended position against the biasing member and the needle is retained in the extended position by a locking catch. When the needle is fully inserted into the animal or living being, an unlocking member is activated by contact with the animal. This releases the locking catch such that the needle is free to move from the extended to the retracted position in response to the force exerted by the spring or biasing member. This movement extracts the needle from the animal leaving the implanted transponder.

Since such injectors are meant in particular to be used by non-medical people such as farmers, it is important that they have a good view as regards the positioning of the needle. It is therefore important that they can see accurately how the needle is placed and how it enters the living being.

The object of the present invention is to avoid these disadvantages.

This object is achieved in the case of the device described above through the fact that the control means are connected to the needle(holder) and are arranged to pretension the spring and lock the needle in the extended position before insertion of the object into the living being, and through the fact that the unlocking means are designed to unlock the needle for returning it to the housing. The invention is based on the idea of moving the needle out with the control means before injecting. For this, two hands are needed, one hand to hold the housing, and the other hand to move the control means. This limits the risk of injuries. Only when the needle has been moved out are the unlocking means brought into play and without further action, i.e. without the intervention of further control means, the needle will be moved back when the skin acts on the unlocking means. Since the needle has already been moved out for the injection, it is necessary for the person inserting the object to place the needle together with the injector in the animal with his own force. This means that very accurate and readily visible positioning of the needle and insertion of the needle are possible, on the one hand, while "feeling" for insertion of the needle in the animal is present, on the other. There are no longer problems with regard to encountering obstacles or easier insertion of the needle in certain cases, while damage to the object to be implanted is prevented. Since the energy for insertion of the needle is produced by pressure on the injector, the spring construction can be made lighter, and less tensioning force is required.

The moment the insertion is completed, the unlocking means will touch the skin of the living being in question, and the needle will move back, with the result that a safe situation is immediately obtained, so that it is no longer possible for undesirable injuries to take place.

According to a preferred embodiment of the invention, the needle is provided so that it is lockable on the needleholder in a simple manner using a push button.

The object to be implanted can be inserted into the hollow needle in two different ways. On the one hand, it is possible in the case of a stationary push rod, i.e. fixed to the housing, to insert the object from the front side of the hollow needle. In this case all that is needed is to and fro movement of the needle relative to the housing and the push rod fixed to it. The unlocking means in this embodiment engage on the needle(holder).

According to another embodiment, the object to be implanted is inserted into a nesting place in the housing. In this case both the needle and the push rod move into the living being, i.e. in a stationary position relative to the housing the hollow needle accommodates the object, and the object is then conveyed by the push rod situated inside the needle. In this embodiment, the unlocking means act on the rear side of the push rod. Blocking devices are present here to lock the needle in the position where it is moved out. By means of a stop fitted on the push rod, said blocking devices can be unlocked, so that the needle together with the push rod can be moved back. The movement in this case takes place in such a way that on operation of the unlocking means the push rod is first moved out with the object, and at the end of the movement path of the push rod through releasing of the blocking devices the needle is moved back together with the push rod, leaving behind the object in position in the animal. According to a special embodiment, provision is made here for the push rod at the end of the movement to position the object near the front end of the needle, so that the object is not pressed into the living being, but the object is placed only by moving back the needle and holding the push rod still during a short stage of the return movement.

According to a further advantageous embodiment, the nesting place is designed to receive a number of objects, and means are present for placing these in succession in front of the push rod in the hollow needle. This means that the objects, such as transponders, can be supplied in cartridges, and that cartridges can always automatically be moved one position further through acting upon the control means. As is generally known in the state of the art, such cartridges can have cavities filled with liquid or ointment, in which the relevant objects are placed. The hollow needle or the push rod in this case easily pierces the ends of the cartridge to be pierced.

BRIEF DESCRIPTION OF THE DRAWINGS

The invention will be explained in greater detail below with reference to examples of embodiments shown in the drawing, in which.

DESCRIPTION OF THE PREFERRED EMBODIMENTS

Figure 1:
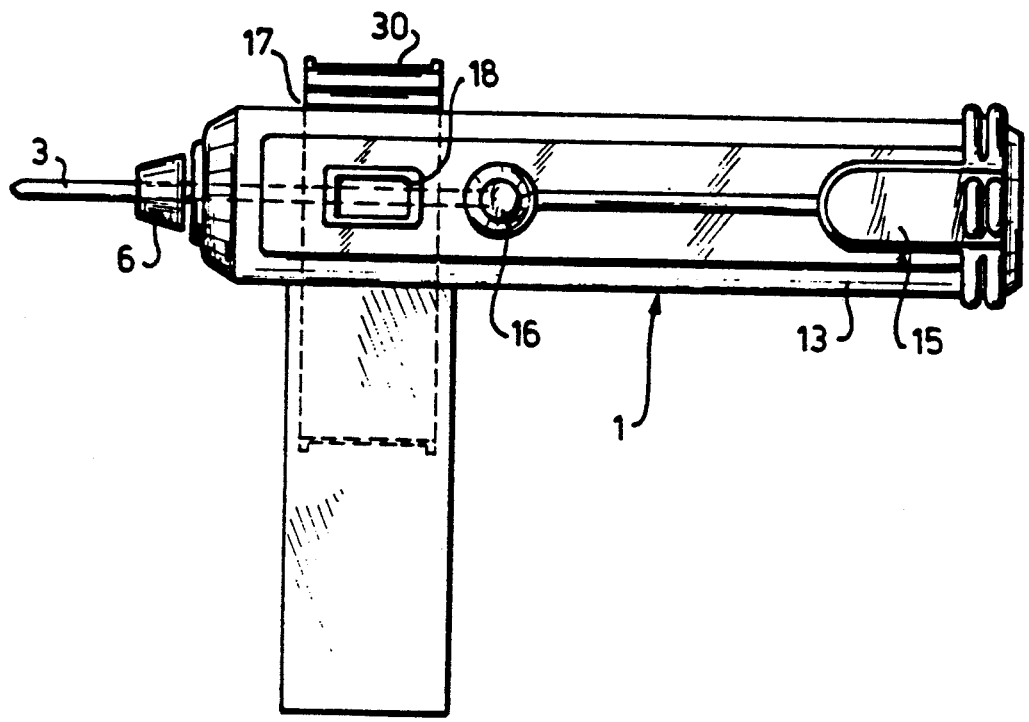
FIG. 1 shows a side view of a first embodiment of the injector according to the invention.

FIG. 1 shows in side view a so-called multi-shot injector. It is indicated in its entirety by 1, and comprises a housing 13 from which projects a control handle 15 which is guided slidably. At the top side of housing 1 a nesting place 17 is present for placing therein a cartridge 30 in which objects 14 to be implanted are accommodated. The position of cartridge 30 with object 14 in it can be observed through inspection window 18. An unlocking catch 6 and also an extended needle 3 are shown at the front side of housing 13.

FIGS. 2a-2e show schematically the mechanism situated in housing 13. As already indicated above, a slidable needle 3 fixed in a needleholder 2 is present. A compression spring 4 acts on needleholder 2 and at the other side acts on the housing. A push rod 9 is present for moving objects 14. Push rod 9 is at one end provided with a push rod plate 10 on which a tension spring 5 acts, which spring is connected at the other side to the needleholder 2. Acting on push rod plate 10 is an unlocking lever 8 which is connected by means of an unlocking rod 7 to unlocking catch 6. Push rod plate 10 is also provided with a stop 11. A blocking device 12 which can act on needleholder 2 is fitted on the housing 1.

Figure 2A:
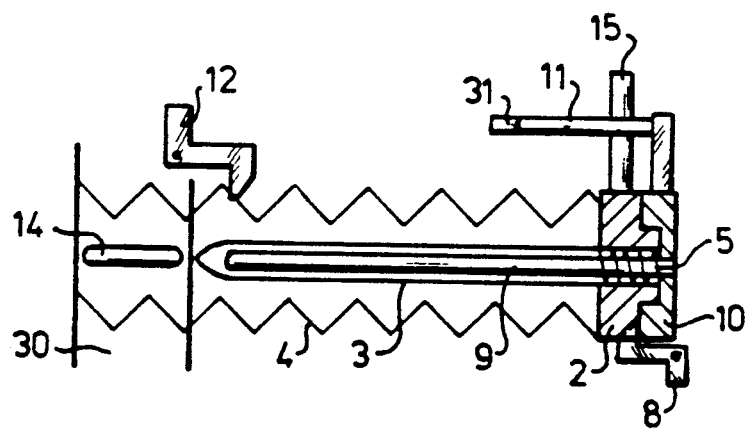
FIGS. 2a-2e show schematically the displacement mechanism for the hollow needle and the push rod in various positions, which displacement mechanism is fitted in the injector according to FIG. 1.

The device described above works as follows:

In the stored position, injector 1 is in the position shown in FIG. 2a, i.e. needle 3 is inside housing 13, so that any risk of accidental injuries is avoided. Cartridge 30 is provided in order to inject an object 14 into a living being. Through inspection window 18 an optical indication is obtained of whether an object 14 is in fact lying in front of needle 3 (FIG. 2a). In the position shown in FIG. 2a the operation of the unlocking catch 6 has no effect at all. For, both springs 4 and 5 are in their untensioned position in FIG. 2a.

Figure 2B:
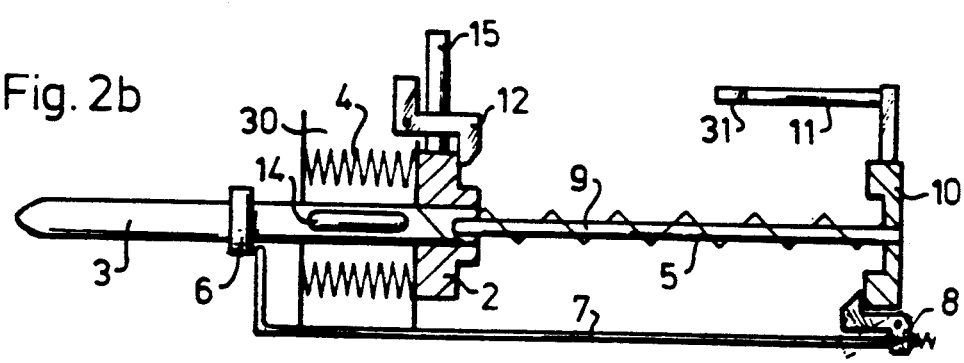

The device is then made ready for the injection of an object 14. For this, the springs 4 and 5 are tensioned by moving control handle 15 to the left out of the position shown in FIG. 2a. Needle 3 will in the process move outwards, and push rod 9 will be held in place through push rod plate 10 being held by unlocking lever 8. After the movement of needleholder 2 along blocking device 12, it can no longer move back by itself. The situation shown in FIG. 2b is reached before the placing of the injector on the animal. For such an operation two hands are needed, one hand to hold the housing 13, and the other hand to move the control handle 15 to the left. In this way injuries from the sharp hollow needle are prevented as far as possible. When needle 3 is moved to the left the cartridge in which object 14 is situated is pierced.

The injector is then moved near an animal, and needle 3 is placed in the animal. All this takes place with manual force, so that the operating person can see and feel well how the needle goes into the animal in question. At the end of insertion of the needle into the animal, unlocking catch 6 is operated through contact with the animal. As shown by dashed lines in FIG. 2b, unlocking lever 8 tilts, so that push rod plate 10 and the push rod are released. This causes push rod 9 to slide to the position shown in FIG. 2c, in which the object to be injected, such as a transponder, is moved to the end of the needle. As can be seen from FIG. 2c, this movement of push rod 9 is continued until stop 11 touches blocking device 12. Further movement to the left is not possible.

Figure 2C:
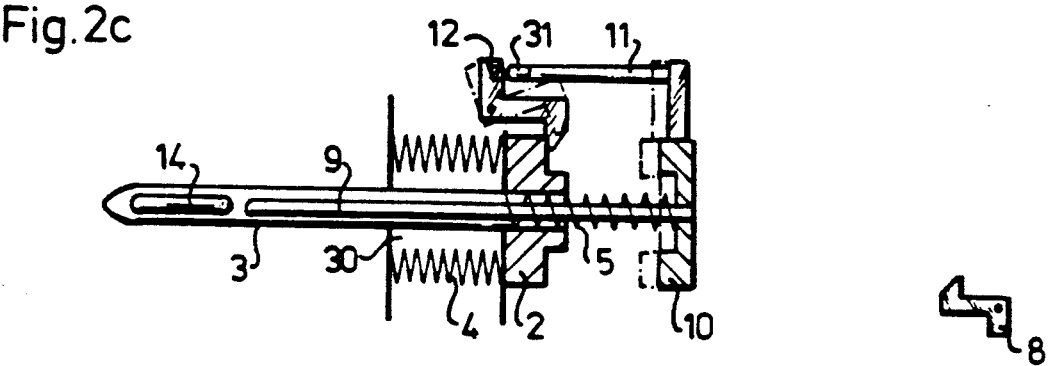

The end position is shown by dashed lines in FIG. 2c. Stop 11 is provided near the end with a softer part 31, in order to make the impact of stop 11 against blocking device 12 take place somewhat gradually.

Figure 2D:
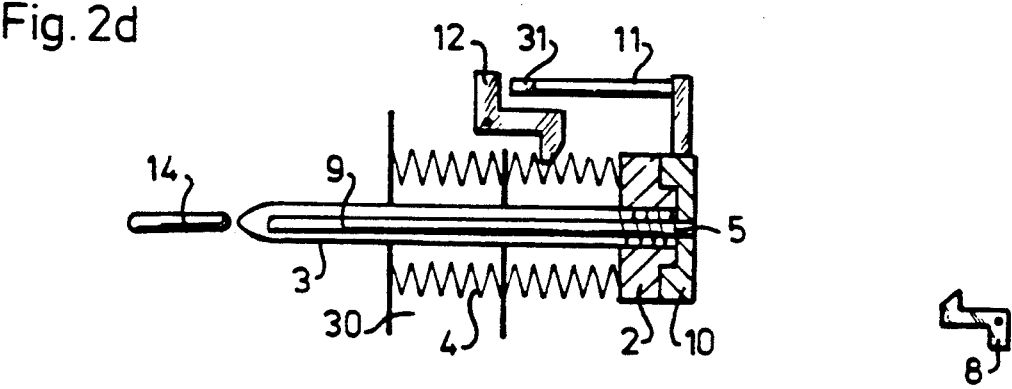
Figure 2E:
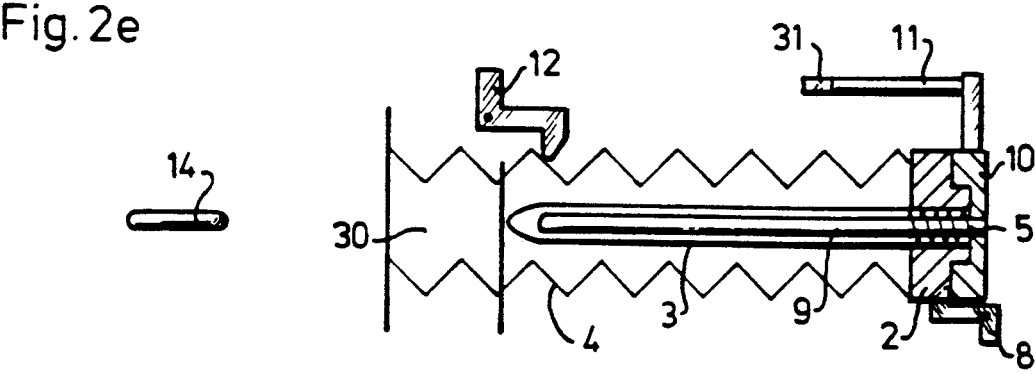

Releasing blocking device 12 causes needleholder 2 to move to the right. This movement is produced by spring 4. Spring 5 still tries to bring push rod plate 10 and needleholder 2 as close together as possible. The result of this is that the object 14, such as a transponder, can never be pushed out of the needle by the push rod 9. Starting from the position shown in FIG. 2c, the needle is withdrawn to the position shown in FIG. 2d, and the push rod 9 remains stationary, with the result that the transponder stays in place, and the needle is moved back. Placing in this way ensures that, on the one hand, tissue damage is avoided and, on the other, damage to the object to be placed is prevented. As shown in FIG. 2d, the needle together with the push rod then moves to the right to the position shown in FIG. 2e, where both parts are safely accommodated in the housing. At the end of this movement or at the beginning of the operation with the aid of control handle 15, a further conveyance mechanism (not shown) can be operated to make cartridge 30 slide one position further.

Figure 3:
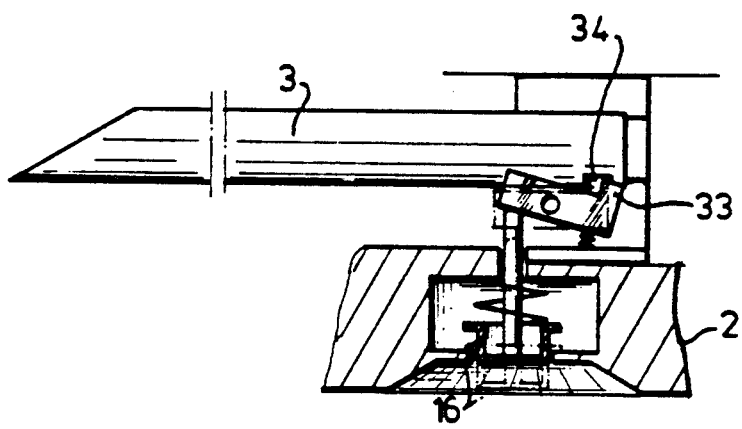
FIG. 3 shows the fixing mechanism of the hollow needle to the needleholder.

In FIG. 3 the fixing of the needle 3 on the needleholder 2 is shown. It can be seen that a push button 16 with a lever mechanism 33 is present. The lobe of the lever in this case falls into a recess 34 provided in the needle. A needle can be removed simply from holder 2 by operating button 16.

FIG. 4 shows a simplified embodiment of the device according to the invention. It is indicated in its entirety by 19 and comprises a housing 25 to which push rod 24 is fixed. Needle 3 is fixed to needleholder 20, which is provided with a control handle part 26, with which the needle can be slid out of the housing. The movement out of the housing is opposed by compression spring 21. As in the case of the preceding embodiments, an unlocking catch 22 is present, forming part of an unlocking lever 23 which acts on needleholder 20.

Figure 4A:
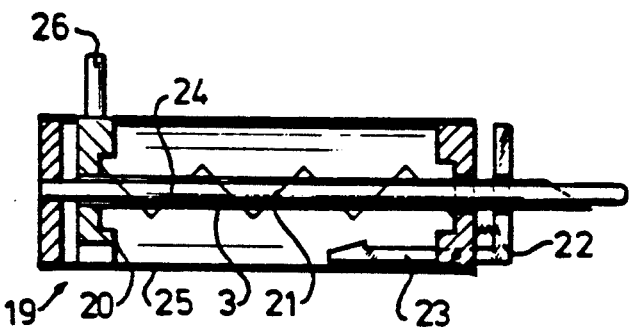
FIG. 4 shows schematically another embodiment of the injector according to the invention.
Figure 4B:
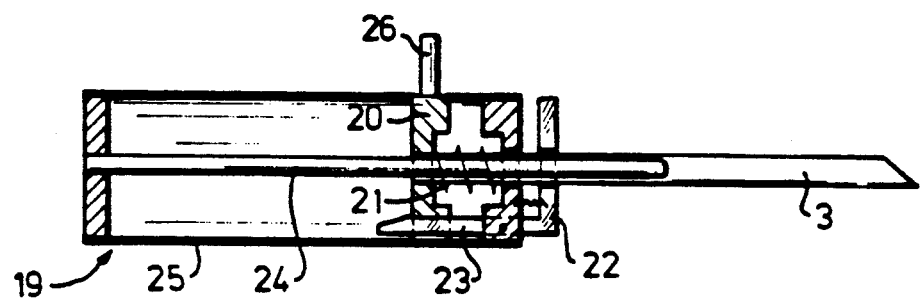
Figure 4C:
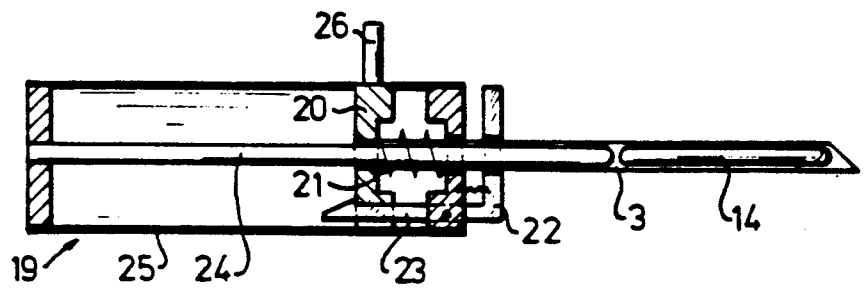
Figure 4D:
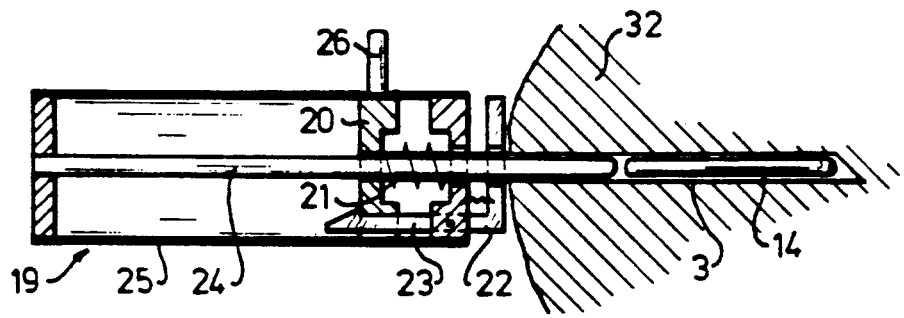
Figure 4E:
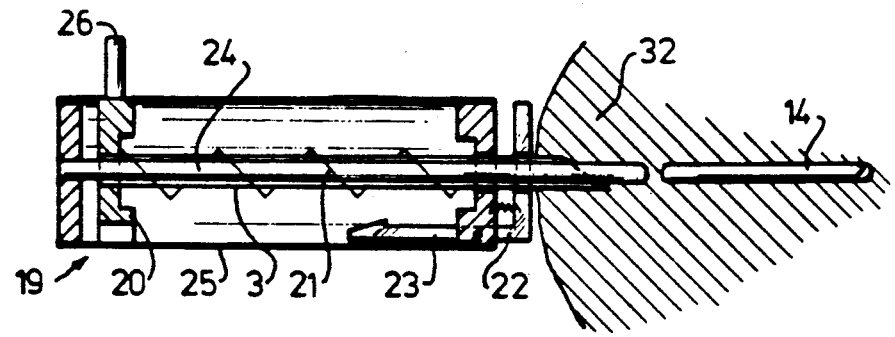

FIG. 4a shows the position of said so-called single-shot injector in the stored position. The needle projects little if at all from the housing. For the use of this injector the needle is moved outwards by means of control handle 26, and the situation shown in FIG. 4b is produced. Needleholder 20 in this case locks behind unlocking lever 23. Then, as shown in FIG. 4c, an object 14 is inserted into the hollow needle. Needle 3 together with the push rod is then pressed into the living being 32. As soon as unlocking catch 22 touches the living being, needleholder 20 will be released from unlocking lever 23, with the result that needle 20 is moved out of the living being 32. The push rod in this case remains in the same place, so that the transponder stays behind in the animal. The injector can then be removed from the animal.

Although the invention is illustrated with reference to two preferred embodiments, it is obvious that numerous modifications can be made without departing from the idea of the invention, namely that the needle is first moved out of the housing by hand and the placing operation of the object to be implanted and the withdrawal of the needle are continued automatically by unlocking means after insertion of the needle into the living being.

We claim:

1. An injector for hypodermically implanting an object in a living being comprising:

a housing;

a hollow needle suitable for delivering said object therethrough and into said living being, said hollow needle having a sharp end and a supported end, said supported end connected to said housing such that said hollow needle slidably moves between a retracted position at least partially within said housing and an extended position at least partially outside of said housing;

a push rod fitted within said hollow needle and operably connected to said housing such that said push rod is maintained in a fixed position during the movement of said hollow needle from said extended position toward said retracted position;

a biasing member connected to said housing and said hollow needle to exert a force so as to urge said needle toward said retracted position;

a control member for manually moving said needle to said extended position against said force of said biasing member;

a first locking catch for retaining said needle in said extended position; and an unlocking member connected to said housing and located such that said unlocking member will contact said living being when said extended needle is fully inserted, and said unlocking member interacting with said first locking catch such that contact of said unlocking member with said living being will release said first locking catch so that said biasing member will urge said needle to said retracted position around said push rod thereby leaving said object implanted within said living being.

2. The injector of claim 1 wherein said push rod is moveable with respect to said housing and further comprising:

a second biasing member for exerting a force to move said push rod from a first position where said push rod is substantially withdrawn from said needle and a second position where said push rod is fully inserted within said needle;

a second locking catch for retaining said push rod in said first position; and wherein said unlocking member further interacts with said second locking catch to release said second latching catch to move said push rod to said second position prior to said unlocking member releasing said first locking catch.

3. The injector of claim 2 and further comprising a cartridge for holding a plurality of objects to be inserted into living beings, said cartridge adapted to be positioned within said housing for feeding objects to be inserted into said needle.

4. The injector of claim 1 and further comprising a needle holder connected to said needle at said supported end and wherein said needle is detachably secured to said needle holder.

* * * * *